US012714695B2

(12) United States Patent
Paz

(10) Patent No.: US 12,714,695 B2
(45) Date of Patent: Aug. 25, 2026

(54) HISTAMINE RECEPTOR AGONISTS FOR CANCER THERAPY IN CANCER PATIENTS UNRESPONSIVE TO CANCER IMMUNOTHERAPY AND WITH ELEVATED MYELOID DERIVED SUPPRESSOR CELLS

(71) Applicant: TSP Therapeutics Inc., Indian Rocks Beach, FL (US)

(72) Inventor: Alberto Paz, Indian Rocks Beach, FL (US)

(73) Assignee: TSP Therapeutics Inc., Indian Rocks Beach, FL (US)

( * ) Notice: Subject to any disclaimer, the term of this patent is extended or adjusted under 35 U.S.C. 154(b) by 314 days.

(21) Appl. No.: 18/425,829

(22) Filed: Jan. 29, 2024

(65) Prior Publication Data

US 2024/0277668 A1 Aug. 22, 2024

Related U.S. Application Data

(63) Continuation of application No. PCT/US2022/035138, filed on Jun. 27, 2022.

(60) Provisional application No. 63/203,813, filed on Jul. 30, 2021.

(51) Int. Cl.

| | |
|---|---|
| ***A61K 31/417*** | (2006.01) |
| ***A61K 9/28*** | (2006.01) |
| ***A61K 38/20*** | (2006.01) |
| ***A61K 45/06*** | (2006.01) |
| ***A61P 35/02*** | (2006.01) |

(52) U.S. Cl.

CPC .............. *A61K 31/417* (2013.01); *A61K 9/28* (2013.01); *A61K 38/2013* (2013.01); *A61K 45/06* (2013.01); *A61P 35/02* (2018.01)

(58) Field of Classification Search

CPC .... A61K 31/417; A61K 9/28; A61K 38/2013; A61K 45/06; A61P 35/02; A61P 35/00; G01N 2800/52

See application file for complete search history.

(56) References Cited

U.S. PATENT DOCUMENTS

| | | | |
|---|---|---|---|
| 6,003,516 | A | 12/1999 | Hellstrand et al. |
| 6,071,509 | A | 6/2000 | Hellstrand et al. |
| 6,071,942 | A | 6/2000 | Hellstrand et al. |
| 6,498,181 | B1 | 12/2002 | Gehlsen et al. |
| 6,528,654 | B2 | 3/2003 | Yeh et al. |
| 6,627,223 | B2 | 9/2003 | Percel et al. |
| 6,663,888 | B2 | 12/2003 | Percel et al. |
| 10,864,166 | B2 | 12/2020 | Venkatesh et al. |
| 2003/0017145 | A1 | 1/2003 | Hellstrand et al. |
| 2005/0171192 | A1 | 8/2005 | Gehlsen |
| 2006/0057197 | A1 | 3/2006 | Han et al. |
| 2007/0128607 | A1 | 6/2007 | Dugas et al. |
| 2008/0317846 | A1 | 12/2008 | Percel et al. |
| 2016/0310559 | A1 | 10/2016 | Fretzen et al. |
| 2017/0065614 | A1 | 3/2017 | Betageri et al. |
| 2019/0240293 | A1 | 8/2019 | Weinstein et al. |
| 2021/0187072 | A1 | 6/2021 | Martner et al. |

FOREIGN PATENT DOCUMENTS

| | | |
|---|---|---|
| EP | 3796911 | 3/2021 |
| WO | WO 2002/033050 A2 | 4/2002 |
| WO | WO 2017/137989 A1 | 8/2017 |
| WO | WO 2019/006133 A1 | 1/2019 |
| WO | WO 2020/033331 A1 | 2/2020 |

OTHER PUBLICATIONS

Extended European Search Report dated Apr. 4, 2022 in European Application No. 19791968.1, in 9 pages.
International Search Report and Written Opinion mailed Sep. 21, 2022 in International Application No. PCT/US2022/035138, in 7 pages.
Bickmore, "Karyotype Analysis and Chromosome Banding Number and Size of Bands", Encyclopedia of Life Sciences, 2001.
Business Wire, "Serametrix MDSC Assay Being Utilized by Infinity Pharmaceuticals in the First Clinical Study to Prospectively Identify Patients With High Blood Levels of MDSCs", Press Release, Carlsbad, California, May 22, 2018.
Cuapio et al., "Maintenance therapy with histamine plus IL-2 induces a striking expansion of two CD 56bright NK cell subpopulations in patients with acute myeloid leukemia and supports their activation", Oncotarget, vol. 7, No. 29, Jun. 21, 2016.
Cellcarta, "MSDC Assays", Brochure, 2020.
Groth et al., "Immunosuppression mediated by myeloid-derived suppressor cells (MDSCs) during tumour progression", British Journal of Cancer, 2019, 120, 16-25.
Hansson et al., "Histamine Protects T Cells and Natural Killer Cells Against Oxidative Stress", Journal of Interferon and Cytokine Research, 19:1135-1144 (1999).
Haslam et al., "Estimation of the Percentage of US Patients With Cancer Who are Eligible for and Respond to Checkpoint Inhibitor Immunotherapy Drugs", Journal of the American Medical Association Network Open, 2019; 2(5): e192535.
Kitano et al., "Computational Algorithm-Driven Evaluation of Monocytic Myeloid-Derived Suppressor Cell Frequency for Prediction of Clinical Outcomes", Cancer Immunology Research, 2014, 2(8), 812-821.
Martner et al., "Histamine Promotes the Development of Monocyte-Derived Dendritic Cells and Reduces Tumor Growth by Targeting the Myeloid NADPH Oxide", Journal of Immunology, 194:5014-5021, prepublished online Apr. 13, 2015.
Mengos et al., "The CD14$^{+}$HLA-DR$^{lo/meg}$ Monocyte: An Immunosuppressive Phenotype That Restrains Responses to Cancer Immunotherapy", Frontiers in Immunology, May 2019, vol. 10, No. 1147, 1-14.

(Continued)

*Primary Examiner* — Kamal A Saeed
*Assistant Examiner* — Meghan C Heasley
(74) *Attorney, Agent, or Firm* — Knobbe, Martens, Olson & Bear, LLP

(57) ABSTRACT

Disclosed herein are formulations of histamine and histamine receptor agonists for treating a cancer or a tumor. Also disclosed are methods of using myeloid derived suppressor cell (MDSC) detection assays to select cancer patients for treatment with the formulations as disclosed herein. Also disclosed are methods of restoring the immune response against tumors in cancer patients who are incomplete responders to immune checkpoint inhibitor (ICI) therapy.

20 Claims, No Drawings

(56) References Cited

OTHER PUBLICATIONS

Nilsson et al., "Immunotherapy with HOC/ IL-2 may be clinically efficacious in acute myeloid leukemia of normal karyotype", Human Vaccines & Immunotherapeutics, Jun. 26, 2019.

Ohl et al., "Reactive Oxygen Species as Regulators of MDSC-Mediated Immune Suppression", Frontiers in Immunology, Oct. 2018, vol. 9, No. 2499, 1-7.

Rieth et al., "Mechanisms of Intrinsic Tumor Resistance to Immunotherapy", International Journal of Molecular Sciences, 2018, 19, 1393-1405.

Wiktorin et al., "Histamine targets myeloid-derived suppressor cells and improves the anti-tumor efficiency of PD-1/PD-I1 checkpoint blockade", Cancer Immunology, Immunotherapy, vol. 68, iss. 2, Oct. 12, 2018, pp. 163-174.

Anonymous: "Maintenance Therapy with Ceplene® (Histamine) and IL-2 on Immune Response and MRD in Acute Myeloid Leukemia", ClinicalTrials.gov, Nov. 29, 2017, XP093292969.

Extended European Search Report dated Jul. 28, 2025, issued in corresponding European Application No. 22850064.1.

Massari et al. "Histamine receptors and cancer pharmacology: an update", British Journal of Pharmacology, vol. 177, No. 3, Dec. 13, 2018, pp. 516-538, XP071172249.

Extended European Search Report dated Mar. 14, 2025, issued in corresponding European Patent Application No. 22805215.5.

International Search Report and Written Opinion dated Oct. 5, 2022, corresponding to International Application No. PCT/US2022/029188.

Ayehunie, S., et al. "Human Primary Cell-Based Organotypic Microtissues for Modeling Small Intestinal Drug Absorption" Pharmaceutical Research (2018) 35(4): 72.

Turco, L. et al. "Caco-2/TC7 cell line characterization for intestinal absorption: How reliable is this in vitro model for the prediction of the oral dose fraction absorbed in human?" Toxicology in Vitro 25 (2011) 13-20.

Stark, H., et al. "Acylated and alkylated histamine derivatives as new histamine H3-receptor antagonists." European journal of medicinal chemistry 29.9 (1994): 695-700.

"Assessment Report for Ceplene." European Medicines Agency (2008) 1-54.

"M9 Biopharmaceutics Classification System-Based Biowaivers, Guidance for Industry." U.S. Department of Health and Human Services, Food and Drug Administration, Center for Drug Evaluation and Research (CDER), Center for Biologics Evaluation and Research (CBER) (May 2021): 1-16.

Evans, et al. "Measurement of gastrointestinal pH profiles in normal ambulant human subjects." Gut 29.8 (1988): 1035-1041.

Islam et al. "A Review on Biodegradable Polymers for Enteric Coating Material." International Journal of Pharmacy & Pharmaceutical Research, Human Journals 6.3 (2016): 141-159.

Jain, et al. "Recent technologies in pulsatile drug delivery systems." Biomatter 1.1 (2011): 57-65.

Pharmapproach.com "Enteric Coating: An Overview." May 16, 2021, www.pharmapproach.com/enteric-coating-2/.

Rewar, et al. "Pulsatile drug delivery system: an overview." Journal of Global Trends in Pharmaceutical Sciences 5.3 (2014): 1943-1955.

Tiligada, et al. "Histamine pharmacology: from Sir Henry Dale to the 21st century." British Journal of Pharmacology 177.3 (2020): 469-489.

Volpe, Donna A. "Application of method suitability for drug permeability classification." The AAPS journal 12.4 (2010): 670-678.

HISTAMINE RECEPTOR AGONISTS FOR CANCER THERAPY IN CANCER PATIENTS UNRESPONSIVE TO CANCER IMMUNOTHERAPY AND WITH ELEVATED MYELOID DERIVED SUPPRESSOR CELLS

CROSS-REFERENCE TO RELATED APPLICATION

This application is a continuation of PCT Application No. PCT/US2022/035138, filed Jun. 27, 2022, which claims priority to and the benefit of U.S. Provisional Patent Application No. 63/203,813, filed Jul. 30, 2021, each of which are incorporated herein by reference. Any and all applications for which a foreign or domestic priority claim is identified in the Application Data Sheet as filed with the present application are hereby incorporated by reference under 37 C.F.R. § 1.57.

BACKGROUND

Field of the Disclosure

The present disclosure relates generally to formulations of histamine and histamine receptor agonists for treating a cancer or a tumor. Also disclosed are methods of using myeloid derived suppressor cell (MDSC) detection assays to select cancer patients for treatment with the formulations as disclosed herein. Also disclosed are methods of restoring the immune response against tumors in cancer patients who are incomplete responders to immune checkpoint inhibitor (ICI) therapy.

Description of the Related Art

The goal of cancer immunotherapy is to successfully stimulate anti-tumor responses and overcome tumor-mediated immunosuppression in cancer patients without the need for chemotherapy. Immunotherapy has the potential to provoke a lymphocyte response that can recognize neoantigens generated by the constantly mutating tumor cells, resulting in a more durable antitumor response than is possible with chemotherapy (Reith, 2018). The optimism created by recent success in cancer immunotherapy has been tempered by sub-optimal clinical responses in the majority of patients with advanced and metastatic tumors. Six immune checkpoint inhibitor (ICI) drugs were approved for 14 indications between Mar. 25, 2011, and Aug. 17, 2018. As a result, the estimated percentage of patients with cancer who are eligible for ICI drugs increased from 1.54% in 2011 to 43.63% in 2018 (Haslam et al., Journal of the American Medical Association Network Open, 2019; 2(5): e192535). However, only 28% of eligible patients are estimated to achieve a complete or partial response to cancer immunotherapy (Haslam ibid).

The impaired anti-tumor immune responses to cancer immunotherapies observed in clinical studies, and in the clinic, in patients with advanced and metastatic tumors are likely a consequence of intrinsic and acquired immune system dysfunctions due to a variety of factors that include, but are not limited to, diminished antigen presentation/detection, leukopenia, a coordinated network of immunosuppressive cell surface proteins, cytokines and cellular mediators (Mengos et al., Frontiers in Immunology, May 2019, Vol. 10, No. 1147, 1-14). The mechanisms of intrinsic tumor resistance most likely involve reducing the quantity and/or quality of anti-tumor lymphocytes (Reith et al., International Journal of Molecular Sciences, 2018, 19, 1393-1405). Meanwhile, acquired resistance to immunotherapy involves mechanisms by which tumor cells develop resistance over the course of treatment, resulting in cancer progression despite an initial treatment response. Several mechanisms have been proposed including the loss of T cell function, the lack of T cell recognition due to immunoediting, and the development of escape mutation variant tumor cells (Reith, ibid).

HLA-DR monocytes are monocytic cells that have a diminished expression, or in some cases no expression, of human leukocyte antigen DR isotype cells. HLA-DR monocytes are also called CD14+HLA-DR$^{low/-}$ monocytes and have emerged as important mediators of tumor-induced immunosuppression. HLA-DR monocytes are part of a larger class of suppressive cells called myeloid derived suppressor cells (MDSCs) which includes monocytic myeloid derived suppressor cells (m-MDSC). An extensive body of literature documents the association of high baseline levels of m-MDSCs with diminished anti-tumor responses and/or poor clinical outcomes with cancer immunotherapies. The evidence shows that m-MDSCs play a role in subverting effective anti-tumor responses, and the abundance of m-MDSCs in a cancer patient's blood inversely correlates with favorable outcomes for cancer patients treated with ICI drugs (Mengos, ibid).

MDSCs are well known to secrete reactive oxygen species (ROS), which are toxic to most cell types and thus contribute to the eradication of tumor-infiltrating lymphocytes. ROS include superoxide anions, hydroxyl radicals, hydrogen peroxide and singlet oxygen. The main pathway of ROS production in MDSCs involves the NADPH oxidase isoforms NOX1, NOX2, NOX3 and NOX4, which transfer electrons from NADPH to oxygen, creating reactive oxygen species (ROS) that include superoxide radicals (Groth et al., British Journal of Cancer, 2019, 120, 16-25). ROS signaling is considered a central mediator of MDSC function and differentiation into anti-tumor lymphocytes. ROS molecules are intrinsically involved in MDSC mediated immune-suppression, as well as activation of transcription factors such as Nrf2 (Nuclear factor erythroid 2-related factor 2) and HIF-1a (Hypoxia-inducible factor 1-alpha), which can induce transcriptional and metabolic reprogramming of MDSCs and influence their differentiation and maintenance (Ohl et al., Frontiers in Immunology, October 2018, Vol. 9, No. 2499, 1-7).

HLA-DR monocytes in the peripheral blood have been designated as m-MDSCs in individual datasets based on their suppression of lymphocyte function and therefore have prognostic value in patients with hematologic cancers (chronic lymphocytic leukemia and multiple myeloma), solid tumors (hepatocellular carcinoma, non-small cell lung cancer, melanoma, and others), and allotransplantation (Kitano et al., Cancer Immunology Research, 2014, 2(8), 812-821). The m-MDSC levels correlate inversely with the presence of NY-ESO-1-specific T cells and appear increased in cancer patients that show no response to an ICI drug. These findings suggest a link between m-MDSCs and antigen-specific immunity in vivo and provide a mechanistic rationale for evaluating m-MDSCs as a biomarker for immunotherapy clinical trials. Presently, there is no established methodology for measuring m-MDSCs as a cancer biomarker. Kitano and coworkers developed a computational analysis of whole blood and cryopreserved samples to measure frequency distribution of m-MDSCs and identified differences in the m-MDSCs populations of pretreatment blood samples between melanoma patients and healthy donors. Melanoma patients with a pretreatment m-MDSC population frequency higher than the healthy donor range from 0 to less than 14.9% were significantly less likely to achieve prolonged overall survival following treatment with an ICI drug. The study used the ICI drug ipilimumab, an antibody that promotes T-cell activation and proliferation. In this patient population, m-MDSC frequencies were inversely correlated with peripheral $CD8^+$ T-cell expansion following ipilimumab. This computational analysis, once confirmed in clinical trials, may enable not only development of a novel pretreatment biomarker for ipilimumab therapy, but also prospective validation of peripheral blood m-MDSCs as a biomarker in multiple disease settings (Kitano ibid).

Furthermore, some histamine receptors are differentially expressed in tumors compared with normal tissues, and this expression is associated with clinicopathological characteristics in most cancer types, suggesting that histamine receptors can be a promising molecular therapeutic target for many types of cancer treatment. However, the availability of pharmaceutical formulations suitable for administration of histamine is limited.

The need exists for an in vivo MDSC detection assay to predict the response of cancer patients to ICI therapy and improve patient outcomes thereby. The need also exists for pharmaceutical formulations capable of administering histamine to cancer patients having a poor prognosis for ICI therapy as predicted by an in vivo MDSC detection assay.

SUMMARY

Several embodiments of the present disclosure relate to pharmaceutical formulations for treating a cancer or a tumor. In several embodiments, the pharmaceutical formulations include a therapeutically effective amount of at least one active pharmaceutical ingredient (API). In several embodiments, the API comprises histamine, a histamine salt, a histamine derivative, a salt of a histamine derivative, and any combination of the foregoing. In several embodiments, the pharmaceutical formulations include a pharmaceutically acceptable carrier, a pharmaceutically acceptable excipient, a pharmaceutically acceptable diluent, and any combination of the foregoing. In several embodiments, the pharmaceutical formulation comprises a dosage form selected from a coated tablet and a liquid form.

In several embodiments, the histamine salt comprises a histamine monocation or a histamine polycation. In several embodiments, the histamine salt comprises at least one anion selected from acetate, aspartate, citrate, formate, fumarate, halide, malate, nitrate, nitrite, phosphite, phosphate, succinate, sulfate, sulfite, tartrate, and any combination of the foregoing. In several embodiments, the histamine salt comprises histamine dihydrochloride. In several embodiments, the histamine derivative comprises a $C_{1-6}$ alkyl histamine. In several embodiments, the histamine derivative comprises N-methylhistamine, 1-methylhistamine, 2-methylhistamine, 4-methylhistamine, 5-methylhistamine, alpha-methylhistamine, and any combination of the foregoing. In several embodiments, the salt of the histamine derivative comprises a $C_{1-6}$ alkyl histamine monocation or a $C_{1-6}$ alkyl histamine polycation. In several embodiments, the salt of the histamine derivative comprises at least one anion selected from acetate, aspartate, citrate, formate, fumarate, halide, malate, nitrate, nitrite, phosphite, phosphate, succinate, sulfate, sulfite, tartrate, and any combination of the foregoing. In several embodiments, the salt of the histamine derivative comprises N-methylhistamine dihydrochloride, 1-methylhistamine dihydrochloride, 2-methylhistamine dihydrochloride, 4-methylhistamine dihydrochloride, 5-methylhistamine dihydrochloride, alpha-methylhistamine dihydrochloride, and any combination of the foregoing.

In several embodiments, the API inhibits the production or release of intracellular hydrogen peroxide.

In several embodiments, the pharmaceutical formulations comprise another therapeutic agent. In several embodiments, the pharmaceutical formulations comprise at least one immune checkpoint inhibitor. In several embodiments, the pharmaceutical formulations comprise at least one cancer immunotherapy agent. In several embodiments, the pharmaceutical formulations comprise at least one cytokine. In several embodiments, the pharmaceutical formulations comprise at least one interleukin.

In several embodiments, a therapeutically effective dosage of the pharmaceutical formulation is from about 0.1 mg to about 500 mg.

In several embodiments, when ingested the pharmaceutical formulation provides a therapeutically effective plasma concentration of the API of equal to or greater than about 0.2 micromole per liter (μmol/L).

In several embodiments, the API is formulated for oral administration. In several embodiments, the API is formulated for parenteral administration. In several embodiments, the API is formulated for subcutaneous administration.

In several embodiments, the pharmaceutical formulations comprise at least one pharmaceutically acceptable carrier. In several embodiments, the pharmaceutical formulations comprise at least one pharmaceutically acceptable excipient. In several embodiments, the pharmaceutical formulations comprise at least one pharmaceutically acceptable diluent.

In several embodiments, the dosage form is provided as coated tablets. In several embodiments, the dosage form is provided in liquid form.

In several embodiments, the pharmaceutical formulations inhibit the growth or delays the onset of melanoma. In several embodiments, the pharmaceutical formulations reduce melanoma tumor size. In several embodiments, the pharmaceutical formulations inhibit the growth or delays the onset of a leukemia. In several embodiments, the pharmaceutical formulations reduce leukemia cancer mass.

Several embodiments of the present disclosure relate to methods for treating a cancer or a tumor. In several embodiments, the methods include selecting or identifying a subject having a population frequency of myeloid derived suppressor cells (MDSC) greater than 3%. In several embodiments, the methods include administering to the subject a pharmaceutical formulation that includes a therapeutically effective amount of at least one active pharmaceutical ingredient (API). In several embodiments, the API includes histamine, a histamine salt, a histamine derivative, a salt of a histamine derivative, and any combination of the foregoing. In several embodiments, the pharmaceutical formulations include a pharmaceutically acceptable carrier, a pharmaceutically acceptable excipient, a pharmaceutically acceptable diluent, and any combination of the foregoing. In several embodiments, the pharmaceutical formulation comprises a dosage form selected from a coated tablet and a liquid form.

In several embodiments, the MDSCs comprise monocytic myeloid derived suppressor cells (m-MDSCs).

In several embodiments, the subject has a cancer or a tumor. In several embodiments, the subject has an incomplete response to checkpoint inhibitor therapy. In several embodiments, the checkpoint inhibitor therapy targets programmed cell death protein 1 (PD-1), programmed death ligand 1 (PD-L1), cytotoxic T-lymphocyte-associated protein 4 (CTLA-4), and any combination of the foregoing In several embodiments, the selecting or identifying is accomplished by a detection assay.

In several embodiments, the method inhibits the production or release of intracellular hydrogen peroxide.

In several embodiments, the methods decrease a level of reactive oxygen species (ROS) within the subject.

In several embodiments, the methods inhibit NADPH oxidase isoform activity.

In several embodiments, the methods avoid inactivation of natural killer cells in the tumor micro-environment. In several embodiments, the methods increase activation of natural killer cells in the tumor micro-environment.

In several embodiments, the methods further comprise administering another therapeutic agent. In several embodiments, the other therapeutic agent is selected from an immune checkpoint inhibitor, a cancer immunotherapy agent, a chemotherapy agent, radiation, surgery, and any combination of the foregoing. In several embodiments, the other therapeutic agent includes an immune checkpoint inhibitor selected from pembrolizumab, nivolumab, ipilimumab, and any combination of the foregoing. In several embodiments, the methods include administering at least one cytokine. In several embodiments, the methods include administering at least one interleukin.

In several embodiments, the pharmaceutical formulation is administered orally. In several embodiments, the pharmaceutical formulation is administered parenterally. In several embodiments, the pharmaceutical formulation is administered subcutaneously.

In several embodiments, the cancer or the tumor is selected from a leukemia, a myeloma, a bone marrow cancer, a Hodgkin's lymphoma, a Non-Hodgkin's lymphoma, a follicular lymphoma, a lymphoid malignancy of T-cell or B-cell origin, a bladder cancer, a brain cancer, a breast cancer, a cervical cancer, a colorectal cancer, an esophageal cancer, a hepatocellular cancer, a melanoma, a head and neck cancer (including oral cancer), an ovarian cancer, a small cell lung cancer, a non-small cell lung cancer, a prostate cancer, a spleen cancer, a polycythemia vera, a thyroid cancer, an endometrial cancer, a stomach cancer, a gallbladder cancer, a bile duct cancer, a testicular cancer, a neuroblastoma, an osteosarcoma, a sarcoma, a carcinoma, an Ewing's tumor and a Wilms's tumor.

In several embodiments, the cancer is a melanoma. In several embodiments, the methods inhibit the growth or delays the onset of melanoma. In several embodiments, the methods reduce a melanoma tumor size.

In several embodiments, the cancer is a leukemia. In several embodiments, the cancer is a leukemia selected from an acute myeloid leukemia, a lymphoblastic leukemia, a myelogenous leukemia, a chronic lymphocytic leukemia, a chronic myeloid leukemia, and any combination of the foregoing. In several embodiments, the methods inhibit the growth or delays the onset of leukemia. In several embodiments, the methods reduce a leukemia tumor size.

DETAILED DESCRIPTION

Introduction

Several embodiments of the present disclosure relate to formulations for treating a cancer or a tumor that include H2 receptor agonists and pharmaceutically acceptable carriers and/or excipients. Specifically, the H2 receptor agonists include histamine dihydrochloride, N-methyl-histamine, 4-methyl-histamine, and histamine phosphate. Additionally disclosed are various dosage forms of the H2 receptor agonist formulations such as coated tablets and liquid forms.

Also disclosed are methods of using myeloid derived suppressor cell (MDSC) detection assays for treating a cancer or a tumor with the H2 receptor agonist formulations. In several embodiments, the methods include FDA-cleared MDSC detection assays that can be interpreted in a centralized Clinical Laboratory Improvement Amendments of 1988 (CLIA) certified MDSC diagnostic laboratory to select cancer patients having an m-MDSC population frequency greater than or equal to 14.9%, defined as the percentage of HLA-DR$^{low/-}$ cells among CD14$^{+}$CD11b$^{+}$ monocytes. The selected cancer patients are incomplete responders to immune checkpoint inhibitor (ICI) therapy. Specifically, the cancer or a tumor can be selected from a melanoma or leukemia.

Several embodiments of the present disclosure provide a method of restoring the immune response against tumors in cancer patients with ROS-mediated suppression of anti-tumor lymphocytes. Also disclosed are methods of restoring the efficacy of immunotherapy and ICI therapy. The present disclosure provides a method for preventing ROS-mediated inactivation of natural killer (NK) and cytotoxic T-cells. Also provided is a method for enhancing ICI-induced propagation and activation of cytotoxic T cells in the presence of elevated levels of m-MDSCs in the tumor micro-environment.

Also disclosed are methods of treating cancer in which an H2 receptor agonist formulation is administered in conjunction with other cancer immunotherapies to increase TCR ζ-chain expression, promote T-cell proliferation, increase the quantity and/or quality of anti-tumor lymphocytes, and promote m-MDSC maturation to neutrophils, macrophage and dendritic cells.

Definitions

The following description provides context and examples, but should not be interpreted to limit the scope of the disclosure covered by the claims that follow in this specification or in any other application that claims priority to this specification. No single component or collection of components is essential or indispensable. For example, some embodiments one or more variables, such as Y or Y and Q may be omitted. Any feature, structure, component, material, step, or method that is described and/or illustrated in any embodiment in this specification can be used with or instead of any feature, structure, component, material, step, or method that is described and/or illustrated in any other embodiment in this specification.

The term "monocation," as used herein is a molecule that is bonded, or otherwise connected, to one proton that is not part of the molecule's essential structure, the molecule has a formal charge of +1. The term "dication," as used herein, is a molecule that is bonded, or otherwise connected, to two protons that are not part of the molecule's essential structure, the molecule has a formal charge of +2. The term "polycation," as used herein, is a molecule that is bonded, or otherwise connected, to two or more protons that are not part of the molecule's essential structure, the molecule has a formal charge that is positive and is equal to the number of protons bonded to the molecule.

The terms "cancer" and "tumor" are used interchangeably herein and shall be given their ordinary meaning and shall also refer to cells which exhibit relatively autonomous growth, so that they exhibit an aberrant growth phenotype characterized by a significant loss of control of cell proliferation. In general, cells of interest for detection or treatment in the present application include precursors, precancerous (e.g., benign), malignant, pre-metastatic, metastatic, and non-metastatic cells.

The term "diagnosis," as used herein shall be given its ordinary meaning and shall also include determination of a subject's susceptibility to a disease or disorder, determination as to whether a subject is presently affected by a disease or disorder, prognosis of a subject affected by a disease or disorder (e.g., identification of cancer or cancerous states, stages of cancer, or responsiveness of cancer to therapy), and use of therametrics (e.g., monitoring a subject's condition to provide information as to the effect or efficacy of therapy).

The terms "plasma profile," "plasma concentration," "$C_{max}$," and "$C_{min}$" as used herein refer to the concentration of drug in the plasma of a subject, generally expressed as mass per unit volume, e.g., nanograms per milliliter (ng/mL), or moles per unit volume, micromole per liter (μmol/L)

The terms "pharmaceutically acceptable salt" and "salt" as used herein refer to a salt of a compound that does not cause significant irritation to an organism to which it is administered and does not abrogate the biological activity and properties of the compound. In several embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, C1-C7 alkylamine, cyclohexylamine, triethanolamine, ethylenediamine, and salts with amino acids such as arginine and lysine.

A "pharmaceutically acceptable carrier" refers to a substance, not itself a therapeutic agent, which may facilitate the incorporation of a compound into cells or tissues. The carrier may be a liquid for the dissolution of a compound to be administered by ingestion. The carrier may be a vehicle for delivery of a therapeutic agent to a subject. The carrier may improve the stability, handling, or storage properties of a therapeutic agent. The carrier may facilitate formation of a dose unit of a composition into a discrete article such as a capsule, tablet, film coated tablet, caplet, gel cap, pill pellet, or bead, and the like suitable for oral administration to a subject.

The term "pharmaceutical composition" or "composition" refers to a mixture of a compound disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and/or salicylic acid. Pharmaceutical compositions will generally be tailored to the specific intended route of administration.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that is physiologically compatible with human cells and tissues.

As used herein, an "excipient" refers to an inert substance that is added to a pharmaceutical composition to provide, without limitation, bulk, consistency, stability, binding ability, lubrication, or disintegrating ability etc., to the composition. A "diluent" is a type of excipient.

As used herein, a "subject" refers to an animal that is the object of treatment, inhibition, or amelioration, observation or experiment. "Animal" includes cold- and warm-blooded vertebrates and/or invertebrates such as fish, shellfish, or reptiles and, in particular, mammals. "Mammal" includes, without limitation, mice, rats, rabbits, guinea pigs, dogs, cats, sheep, goats, cows, horses, primates, such as monkeys, chimpanzees, and/or apes, and, in particular, humans. In some embodiments, the subject is human.

Some embodiments disclosed herein related to selecting a subject or patient in need. In some embodiments, a patient is selected who is in need of treatment of cancer, such as a bladder cancer or a prostate cancer. In some embodiments, a patient is selected who has previously been treated for cancer, such as bladder cancer or prostate cancer. In some embodiments, a patient is selected who has previously been treated for being at risk of cancer, such as bladder cancer or prostate cancer. In some embodiments, a patient is selected who has developed a recurrence of cancer, such as bladder cancer or prostate cancer. In some embodiments, a patient is selected who has developed resistance to therapies for cancer, such as bladder cancer or prostate cancer. In some embodiments, a patient is selected who may have any combination of the aforementioned selection criteria.

The terms "therapeutically effective amount" and "effective amount" refer to the amount of active pharmaceutical ingredient necessary to provide the desired pharmacologic result. In practice, the therapeutically effective amount will vary widely depending on the severity of the disease condition, age of the subject, and the desired therapeutic effect.

The terms "treatment," "treating," "treat," and the like shall be given their ordinary meaning and shall also include herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. The terms "treatment," as used herein shall be given its ordinary meaning and shall also cover any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, e.g., arresting its development; and/or (c) relieving the disease symptom, e.g., causing regression of the disease or symptom.

As used herein, the term "weight percent," when referring to a component, is the weight of the component divided by the weight of the composition that includes the component, multiplied by 100%. For example, the weight percent of component A when 5 grams of component A is added to 95 grams of component B is 5% (e.g., 5 g A/(5 g A+95 g B)×100%).

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the general description and the following detailed description are exemplary and explanatory only and are not restrictive. The term "and/or" denotes that the provided possibilities can be used together or be used in the alternative. Thus, the term "and/or" denotes that both options exist for that set of possibilities.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "comprising" as used herein is synonymous with "including," "containing," or "characterized by," and is inclusive or open-ended and does not exclude additional, unrecited elements or method steps; the term "having" should be interpreted as "having at least;" the term "includes" should be interpreted as "includes but is not limited to;" the term "example" is used to provide exemplary instances of the item in discussion, not an exhaustive or limiting list thereof; and use of terms like "preferably," "preferred," "desired," or "desirable," and words of similar meaning should not be understood as implying that certain features are critical, essential, or even important to the structure or function of the invention, but instead as merely intended to highlight alternative or additional features that may or may not be utilized in a particular embodiment of the disclosure. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Pharmaceutical Formulation

Several embodiments of the present disclosure relate to pharmaceutical formulations for treating a cancer or a tumor. In several embodiments, the pharmaceutical formulations include a therapeutically effective amount of at least one active pharmaceutical ingredient (API). The terms "active pharmaceutical ingredient" and "API" are used interchangeably herein with each other and with the terms "drug" and "therapeutic agent." The term "API" includes both a single API and a combination of several APIs as in cases where the solid dispersion comprises more than one API. As used herein, API includes a distinct compound, pharmaceutically acceptable salts, polymorphs, stereoisomers, solvates, esters, and any combination of the foregoing. In several embodiments, the API includes histamine, a histamine salt, a histamine derivative, a salt of a histamine derivative, and any combination of the foregoing. In some embodiments, the API is histamine. In certain embodiments, the API is a histamine salt. In other embodiments, the API is a histamine derivative. In other embodiments, the API is a salt of a histamine derivative. In several embodiments, the pharmaceutical formulations include a pharmaceutically acceptable carrier, a pharmaceutically acceptable excipient, a pharmaceutically acceptable diluent, and any combination of the foregoing. In several embodiments, the pharmaceutical formulation comprises a dosage form selected from a coated tablet and a liquid form.

In several embodiments, the histamine salt comprises a histamine monocation, a histamine polycation, and any combination of the foregoing. In several embodiments, the histamine salt comprises a histamine dication. In several embodiments, the histamine salt comprises at least one anion selected from acetate, aspartate, citrate, formate, fumarate, halide, malate, nitrate, nitrite, phosphite, phosphate, succinate, sulfate, sulfite, tartrate, and any combination of the foregoing. In several embodiments, the histamine salt comprises histamine dihydrohalide or histamine phosphate. In several embodiments, the histamine salt comprises histamine dihydrochloride.

The term "histamine derivative," as used herein, is a structural analog of histamine and/or a synthetically derived analog of histamine. In several embodiments, the histamine derivative comprises $C_{1-6}$ alkyl histamine. In some embodiments, the histamine derivative comprises N—($C_{1-6}$ alkyl) histamine, 1-($C_{1-6}$ alkyl)histamine, 2-($C_{1-6}$ alkyl)histamine, 4-($C_{1-6}$ alkyl)histamine, 5-($C_{1-6}$ alkyl)histamine, alpha-($C_{1-6}$ alkyl)histamine, and any combination of the foregoing. In several embodiments, the histamine derivative comprises N-methylhistamine, 1-methylhistamine, 2-methylhistamine, 4-methylhistamine, 5-methylhistamine or alpha-methylhistamine. In several embodiments, the histamine derivative comprises N-methylhistamine. In several embodiments, the histamine derivative comprises alpha-methylhistamine.

In several embodiments, the salt of the histamine derivative comprises $C_{1-6}$ alkyl histamine monocation, $C_{1-6}$ alkyl histamine polycation and any combination of the foregoing. In several embodiments, the salt of the histamine derivative comprises $C_{1-6}$ alkyl histamine dication. In several embodiments, the salt of the histamine derivative comprises N—($C_{1-6}$ alkyl)histamine dication, 1-($C_{1-6}$ alkyl)histamine dication, 2-($C_{1-6}$ alkyl)histamine dication, 4-($C_{1-6}$ alkyl)histamine dication, 5-($C_{1-6}$ alkyl)histamine dication, alpha-($C_{1-6}$ alkyl)histamine dication, and any combination of the foregoing. In several embodiments, the salt of the histamine derivative comprises at least one anion selected from acetate, aspartate, citrate, formate, fumarate, halide, malate, nitrate, nitrite, phosphite, phosphate, succinate, sulfate, sulfite, tartrate, and any combination of the foregoing. In several embodiments, the salt of the histamine derivative comprises N-methylhistamine dihydrochloride, 1-methylhistamine dihydrochloride, 2-methylhistamine dihydrochloride, 4-methylhistamine dihydrochloride, 5-methylhistamine dihydrochloride, alpha-methylhistamine dihydrochloride, and any combination of the foregoing. In several embodiments, the salt of the histamine derivative comprises N-methylhistamine dihydrochloride. In several embodiments, the salt of the histamine derivative comprises alpha-methylhistamine dihydrochloride.

In some embodiments, the API includes at least one histamine receptor agonist. In several embodiments, the histamine receptor agonist is selected from the group consisting of a histamine H1 receptor agonist, a histamine H2 receptor agonist, a histamine H3 receptor agonist, a histamine H4 receptor agonist, and any combination of the foregoing. In several embodiments, the API is a histamine H2 receptor agonist. In certain embodiments, the API does not include an antihistamine. In other embodiments, the API does not include a histamine receptor antagonist. In several embodiments, the API does not include an H1 receptor antagonist, an H2 receptor antagonist, an H3 receptor antagonist, an H4 receptor antagonist, and any combination of the foregoing. In several embodiments, the API includes at least one histamine structural analog having H2 receptor agonist activity.

In several embodiments, the API inhibits the production or release of intracellular hydrogen peroxide. In several embodiments, the API inhibits the production or release of intracellular hydrogen peroxide by monocytes. In several embodiments, the plasma concentration of the API is sufficient to inhibit the production or release of intracellular hydrogen peroxide by monocytes. In an embodiment, the inhibition occurs when the API binds histamine H2 receptors. In several embodiments, the inhibition occurs when the API binds histamine H2 receptors selectively. In several embodiments, the API has an affinity for histamine H2 receptors that is higher compared to the affinity for any other histamine receptor. In several embodiments, the API has affinity for histamine H2 receptors that is higher compared to the affinity for a H1 receptor, a H3 receptor, a H4 receptor, and any combination of the foregoing.

In several embodiments, the pharmaceutical formulations of the present disclosure include another therapeutic agent. The therapeutic agent can be selected from an immune checkpoint inhibitor, a cancer immunotherapy agent, a chemotherapy agent, radiation, and any combination of the foregoing.

In several embodiments, the pharmaceutical formulations comprise at least one immune checkpoint inhibitor. It will be appreciated that some cancers stimulate inhibitory immune checkpoints to create a defense against attack by the immune system. The term "immune checkpoint," as used herein, is a key regulator or inhibitor of the immune system that when stimulated can dampen the immune response. The immune checkpoint can be selected from programmed cell death protein 1 (PD-1), programmed death ligand 1 (PD-L1), cytotoxic T-lymphocyte-associated protein 4 (CTLA-4), and any combination of the foregoing. The term "immune checkpoint inhibitor," as used herein, is a chemical compound (e.g., small molecule) or other entity that blocks, or otherwise inhibits, one or more immune checkpoints to restore proper function of the immune system. In several embodiments, the immune checkpoint inhibitor can be a chemical compound (e.g., small molecule) or other entity that targets (i.e., blocks or otherwise inhibits) PD-1, PD-L1, CTLA-4, and any combination of the foregoing In several embodiments, the immune checkpoint inhibitor can be selected from pembrolizumab, nivolumab, ipilimumab, and any combination of the foregoing.

In several embodiments, the pharmaceutical formulations include at least one cancer immunotherapy agent. In several embodiments, the cancer immunotherapy agent can be selected from cytokines and interleukins. In several embodiments, the pharmaceutical formulations include at least one cytokine. The cytokine can be selected from chemokines, interferons, interleukins, lymphokines, tumor necrosis factors, and any combination of the foregoing. In several embodiments, the pharmaceutical formulations include at least one interleukin. The interleukin can be selected from IL-1, IL-1α, IL-1β, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, and any combination of the foregoing.

The pharmaceutical formulations include a therapeutically effective dosage of at least one active pharmaceutical ingredient (API). In several embodiments, the therapeutically effective dosage of the API in units of milligrams (mg) is equal to or less than about: 0.01, 0.03, 0.07, 0.1, 0.2, 0.3, 0.4, 0.5, 0.6, 0.7, 0.8, 0.9, 1, 1.1, 1.3, 1.6, 2, 3, 5, 8, 10, 15, 18, 20, 30, 50, 100, 200, 3000, 400, 500, 800, 1000, or ranges including and/or spanning the aforementioned values. In several embodiments, the therapeutically effective dosage of the API is from about 0.1 mg to about 200 mg, or from about 0.5 mg to about 100 mg.

In several embodiments, when ingested the pharmaceutical formulations provide a therapeutically effective plasma concentration of the API measured in micromole per liter in (μmol/L) equal to or greater than about 0.01, 0.05, 0.1, 0.15, 0.17, 0.18, 0.19, 0.2, 0.21, 0.22, 0.23, 0.24, 0.25, 0.3, 0.5, 1, 2, 5, 10, 20, 50, 100, or ranges including and/or spanning the aforementioned values. In several embodiments, when ingested the pharmaceutical formulations provide a therapeutically effective plasma concentration of the API equal to or greater than about 0.2 micromole per liter (μmol/L). In several embodiments, when ingested the pharmaceutical formulations provide the therapeutically effective plasma concentration of the API for equal to or greater than about 0.1, 0.25, 0.5, 0.75, 1, 1.25, 1.5, 1.75, 2, 2.25, 2.5, 3, 3.5, 4, 4.5, 5, 6, 7, 8, 9, 10 h, or ranges including and/or spanning the aforementioned values. In several embodiments, when ingested the pharmaceutical formulations provide the therapeutically effective plasma concentration of the API for about 0.25 to about 5 h, or about 0.5 to about 3 h, or about 0.5 to about 1.25 h. The therapeutically effective plasma concentration of the API is determined in accordance with United States Pharmacopoeia (USP) dissolution methodology using a two-stage dissolution medium (first 2 hours in 0.1N HCl followed by testing in a buffer at pH 6.8). In some embodiments, a modeling exercise is typically performed using the pharmacokinetic parameters for the drug using the software program, WinNonlin™ Standard Version 2.1 or equivalent (e.g., GastroPlus™ to fit a 1-compartment first order model with a lag time assuming first order elimination kinetics. The primary parameters are then input into another program, Stella Version 6.01 using a previously established model with slight modifications. Different in vitro release profiles are generated, and from target once-daily release profiles, desired in vitro release (medium, target and fast) profiles are generated by deconvolution.

A. Routes of Administration

The API of the present disclosure, alone or in combination with another therapeutic agent, as described elsewhere herein, may be formulated for oral, intranasal, or parenteral administration. Oral administration may include formulations for administration to the oral cavity, including for administration to the digestive tract, the buccal lining, or the respiratory tract through the oral cavity, for example, formulations as a tablet, pill, capsule, pellet, dragee, gummy, powder, softgel, liquid, syrup, suspension, solution, or inhalant. Intranasal administration may include formulation for administration by the nasal cavity, and may include drops, spray, insufflation, or inhalable formulations. Parenteral administration may include, for example, intraperitoneal, infusion, intramuscular, subcutaneous, intradermal, or intravenous injection.

In several embodiments, the API is formulated for oral administration. In several embodiments, the API is formulated for oral administration in combination with another therapeutic agent.

In several embodiments, the API is formulated for parenteral administration. In several embodiments, the API is formulated for parenteral administration in combination with another therapeutic agent.

In several embodiments, the API is formulated for subcutaneous administration. In several embodiments, the API is formulated for subcutaneous administration in combination with another therapeutic agent.

In some embodiments, the formulations described herein further include pharmaceutically acceptable carriers and excipients, depending on the desired delivery or mode of administration format.

B. Carriers

In several embodiments, the pharmaceutical formulations comprise at least one pharmaceutically acceptable carrier. In some embodiments, the pharmaceutically acceptable carrier may comprise glycerol. In some embodiments, the pharmaceutically acceptable carrier may comprise a mixture of triacylglycerols, monoacylglycerols, diacylglycerols, and/or free fatty acids. In some embodiments, the pharmaceutically acceptable carrier may comprise a mixture of triacylglycerols. In some embodiments, the pharmaceutically acceptable carrier may comprise a mixture of long chain (C8-C50) saturated or unsaturated fatty acids, fatty alcohols, or glyceryl esters of one or more fatty acids. In some embodiments, the long chain saturated or unsaturated fatty acids may comprise from 10 to 40 carbon atoms (C10-C40). In some embodiments, the long chain saturated or unsaturated fatty acids may comprise from 10 to 20 carbon atoms (C10-C20). The mixture of triacylglycerols, monoacylglycerols, diacylglycerols, and/or free fatty acids can be an oil or wax at room temperature.

In some embodiments, each long chain saturated or unsaturated fatty acid is selected from caproic acid, caprylic acid, capric acid, lauric acid, myristic acid, palmitic acid, stearic acid, oleic acid, linolenic acid (including alpha-linolenic acid and/or gamma-linolenic acid), linoleic acid, arachidic acid, ricinoleic acid, dihydroxystearic acid, behenic acid, ligoceric acid, erucic acid, and/or godonic acid. In some embodiments, each long chain saturated or unsaturated fatty acid is selected from (Z)-9-octadecenoic acid, oleic acid (8CI), 9-cis-octadecenoic acid, 9Z-octadecenoic acid, B 115, Clear FRAC EF, Crodacid O-P, Crossential O 94, D 100, D 100 (fatty acid), Edenor ATiO5, Edenor FTiO5, Emersol 205, Emersol 211, Emersol 213NF, Emersol 214NF, Emersol 233, Emersol 6313NF, Extra Oleic 80R, Extra Oleic 90, Extra Oleic 99, Extra Olein 80, Extra Olein 90, Extra Olein 90R, Extra Olein A 1981, Industrene 105, Lunac O-CA, Lunac O-LL, Lunac O-P, Lunac O-V, Lunac OA, NAA 35, NAA 38, Neo-Fat 92-04, Oleine 7503, Pamolyn 100, Priolene 6204, Priolene 6906, Priolene 6907, Priolene 6928, Priolene 6930, Priolene 6933, Vopcolene 27, Wecoline OO, and/or cis-oleic acid.

In some embodiments, the pharmaceutically acceptable carrier may comprise a mixture of triacylglycerols having long chain saturated or unsaturated fatty acids including alpha-linolenic acid, arachidic acid, behenic acid, capric acid, caproic acid, caprylic acid, dihydroxystearic acid, erucic acid, gondonic acid, lauric acid, lignoceric acid, linoleic acid, myristic acid, oleic acid, palmitic acid, palmitoleic acid, ricinoleic acid, and/or stearic acid. In some embodiments, the pharmaceutically acceptable carrier may comprise a mixture of triacylglycerols obtained from the seeds of *Ricinus communis* L., Euphorbiaceae; *Gossypium herbaceum* L., Malvaceae; *Vitis vinifera* L., Vitaceae; *Arachis hypogaea* L., Leguminosae; *Brassica napus* L., Brassicaceae; *Brassica rapa* L., Brassicaceae; *Brassica juncca* L., Brassicaceae; *Helianthus annuus* L., Compositae; *Carthamus tinctorius* L., Compositae; *Sesamum indicum* L., Pedaliaceae; or *Glycine max* L., Fabaceae; or obtained from the kernels of *Cocos nucifera* L., Palmae; or obtained from the grain of *Zea mays* L., Gramincae; or obtained from the fruit of *Olea europaea* L, Oleaceae; *Elaeis guineensis*, Arecaceae; *Elaeis oleifera*, Arecaceae; or *Attalea maripa*, Arecaceae, or any combinations thereof. In some embodiments, pharmaceutically acceptable carrier may comprise a mixture of triacylglycerols, where the mixture of triacylglycerols have a fatty acid content comprising 44-75% linoleic acid, 14-35% oleic acid, 3-10% palmitic acid, 1-8% stearic acid, 0.6-4% arachidic acid, and 1% behenic acid.

In some embodiments, the pharmaceutically acceptable carrier may comprise an oil selected from castor oil, coconut oil, corn oil, cottonseed oil, grapeseed oil, olive oil, palm oil, peanut oil, rapeseed oil, canola oil, safflower oil, sesame oil, soybean oil, or sunflower oil, or any combinations thereof.

In some embodiments, the pharmaceutically acceptable carrier may comprise a mixture of triacylglycerols and further comprise dimethyl sulfoxide. Dimethyl sulfoxide may be used as a pharmaceutically acceptable carrier to facilitate the uptake of the API, alone or in combination with an additional therapy as described herein, into cells or tissues of a subject. Dimethyl sulfoxide may be used as a pharmaceutically acceptable carrier to facilitate absorption of the API in the gastrointestinal tract of a subject.

In some embodiments, the pharmaceutically acceptable carrier may comprise propylene glycol. In some embodiments, the pharmaceutically acceptable carrier may comprise esters of propylene glycol. In some embodiments, the ester of propylene glycol can be propylene glycol monocaproate, propylene glycol monocaprylate, propylene glycol monodecanoate, propylene glycol monolaurate, propylene glycol monomyristate, propylene glycol monopalmitate, propyleneglycol monostearate, propylene glycol monooleate, propylene glycol monolinolenate, propylene glycol dicaproate, propylene glycol dicaprylate, propylene glycol didecanoate, propylene glycol dilaurate, propylene glycol dimyristate, propylene glycol dipalmitate, propyleneglycol distearate, propylene glycol dioleate, or propylene glycol dilinolenate, or any combinations thereof. In some embodiments, the pharmaceutically acceptable carrier may comprise propylene carbonate. In some embodiments, the pharmaceutically acceptable carrier may comprise Capryol™ 90, which is propylene glycol monocaprylate.

In some embodiments, the pharmaceutically acceptable carrier may comprise esters of polyethylene glycol. In some embodiments, the ester of polyethylene glycol can comprise PEG-8, PEG-10, PEG-25, PEG-55, PEG 75, PEG 120, or PEG 660 monocaproate or dicaproate; PEG-8, PEG-10, PEG-25, PEG-55, PEG 75, PEG 120, or PEG 660 monocaprylate or dicaprylate; PEG-8, PEG-10, PEG-25, PEG-55, PEG 75, PEG 120, or PEG 660 monodecanoate or didecanoate; PEG-8, PEG-10, PEG-25, PEG-55, PEG 75, PEG 120, or PEG 660 monolaurate or dilaurate; PEG-8, PEG-10, PEG-25, PEG-55, PEG 75, PEG 120, or PEG 660 monomyristate or dimyristate; PEG-8, PEG-10, PEG-25, PEG-55, PEG 75, PEG 120, or PEG 660 monopalmitate or dipalmitate; PEG-8, PEG-10, PEG-25, PEG-55, PEG 75, PEG 120, or PEG 660 monostearate or distearate; PEG-8, PEG-10, PEG-25, PEG-55, PEG 75, PEG 120, or PEG 660 monooleate or dioleate; PEG-8, PEG-10, PEG-25, PEG-55, PEG 75, PEG 120, or PEG 660 monolinolenate or dilinolenate; or any combination thereof. In some embodiments, the pharmaceutically acceptable carrier may comprise diethylene glycol monoethyl ether.

In some embodiments, the pharmaceutically acceptable carrier may comprise a pegylated glyceride. Exemplary pegylated glycerides comprise GELUCIRE® 44/14 (lauroyl macrogol-32 glycerides) and/or GELUCIRE® 50/13 (stearoyl macrogol-32 glycerides).

In some embodiments, the pharmaceutically acceptable carrier may comprise a fatty acid ester having the general formula R1-C(═O)—O—R2, where R1 and R2 are each saturated or unsaturated C8-C50 hydrocarbons optionally substituted with one or more hydroxyl groups. In some embodiments, each of R1 and R2 can be the same. In some embodiments, each of R1 and R2 can be different. In some embodiments, the fatty acid ester can be methyl caproate, ethyl caproate, propyl caproate, isopropyl caproate, butyl caproate, sec-butyl caproate, tert-butyl caproate, pentyl caproate, hexyl caproate, heptyl caproate, octyl caproate, nonyl caproate, or decyl caproate, or any combination thereof. In some embodiments, the fatty acid ester can be methyl caprylate, ethyl caprylate, propyl caprylate, isopropyl caprylate, butyl caprylate, sec-butyl caprylate, tert-butyl caprylate, pentyl caprylate, hexyl caprylate, heptyl caprylate, octyl caprylate, nonyl caprylate, or decyl caprylate, or any combination thereof. In some embodiments, the fatty acid ester can be methyl decanoate, ethyl decanoate, propyl decanoate, isopropyl decanoate, butyl decanoate, sec-butyl decanoate, tert-butyl decanoate, pentyl decanoate, hexyl decanoate, heptyl decanoate, octyl decanoate, nonyl decanoate, or decyl decanoate, or any combination thereof. In some embodiments, the fatty acid ester can be methyl laurate, ethyl laurate, propyl laurate, isopropyl laurate, butyl laurate, sec-butyl laurate, tert-butyl laurate, pentyl laurate, hexyl laurate, heptyl laurate, octyl laurate, nonyl laurate, or decyl laurate, or any combination thereof. In some embodiments, the fatty acid ester can be methyl myristate, ethyl myristate, propyl myristate, isopropyl myristate, butyl myristate, sec-butyl myristate, tert-butyl myristate, pentyl myristate, hexyl myristate, heptyl myristate, octyl myristate, nonyl myristate, or decyl myristate, or any combination thereof. In some embodiments, the fatty acid ester can be methyl palmitate, ethyl palmitate, propyl palmitate, isopropyl palmitate, butyl palmitate, sec-butyl palmitate, tert-butyl palmitate, pentyl palmitate, hexyl palmitate, heptyl palmitate, octyl palmitate, nonyl palmitate, or decyl palmitate, or any combination thereof. In some embodiments, the fatty acid ester can be methyl stearate, ethyl stearate, propyl stearate, isopropyl stearate, butyl stearate, sec-butyl stearate, tert-butyl stearate, pentyl stearate, hexyl stearate, heptyl stearate, octyl stearate, nonyl stearate, or decyl stearate, or any combination thereof. In some embodiments, the fatty acid ester can be methyl oleate, ethyl oleate, propyl oleate, isopropyl oleate, butyl oleate, sec-butyl oleate, tert-butyl oleate, pentyl oleate, hexyl oleate, heptyl oleate, octyl oleate, nonyl oleate, or decyl oleate, or any combination thereof. In some embodiments, the fatty acid ester can be methyl linolenate, ethyl linolenate, propyl linolenate, isopropyl linolenate, butyl linolenate, sec-butyl linolenate, tert-butyl linolenate, pentyl linolenate, hexyl linolenate, heptyl linolenate, octyl linolenate, nonyl linolenate, or decyl linolenate, or any combinations thereof.

In some embodiments, the pharmaceutically acceptable carrier may comprise a sorbitan ester. In some embodiments, the sorbitan ester can comprise sorbitan monolaurate, sorbitan monopalmitate, sorbitan monostearate, sorbitan monooleate, sorbitan sesquioleate, sorbitan trioleate, or sorbitan isostearate, or any combinations thereof. In some embodiments, the sorbitan ester can comprise Span 20, Span 40, Span 60, Span 80, Span 83, Span 85, Span 120, or any combination thereof.

In some embodiments, the pharmaceutically acceptable carrier may comprise a polysorbate. In some embodiments, the polysorbate can comprise polyoxyethylene (20) sorbitan monolaurate, polyoxyethylene (20) sorbitan monopalmitate, polyoxyethylene (20) sorbitan monostearate, polyoxyethylene (20) sorbitan monooleate, polyoxyethylene (4) sorbitan monolaurate, polyoxyethylene (4) sorbitan monopalmitate, or polyoxyethylene (4) sorbitan monostearate, or polyoxyethylene (4) sorbitan monooleate, or any combinations thereof. In some embodiments, the polysorbate can comprise Tween 20, Tween 21, Tween 40, Tween 60, Tween 61, Tween 65, or Tween 80, or any combination thereof.

In some embodiments, the concentration of the API dissolved or suspended in the at least one pharmaceutically acceptable carrier that comprises a mixture of triacylglycerols, monoacylglycerols, diacylglycerols, and/or free fatty acids may vary from about or any number in between 1-1000 mg of the API per mL of pharmaceutically acceptable carrier. In some embodiments, the concentration of the API ranges from 1, 2, 5, 7, 10, 12, 15, 17, 20, 22, 25, 27, 30, 32, 35, 37, 40, 42, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 275, 300, 325, 350, 375, 400, 425, 450, 475, 500, 525, 550, 575, 600, 650, 700, 750, 800, 850, 900, 950, or 1000 mg/mL or within a range defined by any two of the aforementioned values.

In some embodiments, the concentration of a therapy agent that is used in combination with the API ranges from 1, 2, 5, 7, 10, 12, 15, 17, 20, 22, 25, 27, 30, 32, 35, 37, 40, 42, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 275, 300, 325, 350, 375, 400, 425, 450, 475, 500, 525, 550, 575, 600, 650, 700, 750, 800, 850, 900, 950, or 1000 mg/mL or within a range defined by any two of the aforementioned values.

C. Excipients

In several embodiments, the pharmaceutical formulations comprise at least one pharmaceutically acceptable excipient. Some embodiments disclosed herein include a pharmaceutical formulation comprising the API, at least one pharmaceutically acceptable carrier, and at least one pharmaceutically acceptable excipient. The at least one pharmaceutically acceptable excipient can be selected from a sugar, a starch, a cellulose preparation, silicon dioxide aerosol, gelatin, calcium phosphate dibasic, sodium lauryl sulfate, magnesium stearate, sodium stearyl fumarate, talc, polyethylene glycol, or polyvinylpyrrolidone, or any combinations thereof. In one embodiment, the at least one pharmaceutically acceptable excipient can be selected from a pregelatinized starch, partially pregelatinized starch, microcrystalline cellulose, silicified microcrystalline cellulose, a lactose-cellulose blend, methyl cellulose, or silicon dioxide aerosol, or any combinations thereof. In one embodiment, the at least one pharmaceutically acceptable excipient can be selected from microcrystalline cellulose, lactose, sucrose, starch powder, maize starch or derivatives thereof, cellulose esters of alkanoic acids, cellulose alkyl esters, stearic acid, magnesium oxide, sodium and/or calcium salts of phosphoric and sulfuric acids, acacia gum, sodium alginate, or polyvinyl alcohol, or any combinations thereof. In one embodiment, the at least one pharmaceutically acceptable excipient can be selected from dextrose, mannitol, lactose monohydrate, lecithin, albumin, sodium glutamate, cysteine hydrochloride, croscarmellose sodium, sodium starch glycolate, hydroxypropyl cellulose, poloxamer, sodium lauryl sulfate, or colloidal silicon dioxide, or any combination thereof. Poloxamers comprise, for example, poloxamer 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, 407, poloxamer 105 benzoate, or poloxamer 182 dibenzoate 407 or any combination thereof. In one embodiment, the at least one pharmaceutically acceptable excipient can comprise microcrystalline cellulose. In one embodiment, the at least one pharmaceutically acceptable excipient can be an aluminometasilicate, such as sodium aluminometasilicate, magnesium aluminometasilicate, calcium aluminometasilicate, potassium aluminometasilicate, or lithium aluminometasilicate or any combination thereof.

The amount of the pharmaceutically acceptable excipient may vary from or any number in between 1% to 75% by weight of the total pharmaceutical formulation. In some embodiments, the amount of excipient ranges from or any number in between 1-5%, 2-7%, 5-10%, 7-12%, 10-15%, 12-17%, 15%-20%, 17%-22%, 20%-25%, 22%-27%, 25%-30%, 27%-32%, 30%-35%, 32%-37%, 35%-40%, 37%-42%, 40%-45%, 40-50%, 45-55%, 50-60%, 55-65%, 60-70%, or 65-75% by weight of the total pharmaceutical formulation or within a range defined by any two of the aforementioned amounts. In some embodiments, the amount of excipient is at least 5%, at least 10%, at least 15%, at least 20%, at least 25%, at least 30%, at least 40%, at least 50%, at least 60%, at least 70%, or at least 75% of the weight of the total pharmaceutical formulation or within a range defined by any two of the aforementioned amounts. In some embodiments, the amount of excipient is less than 5% of the weight of the total pharmaceutical formulation but not zero.

The amounts of excipient can be determined by the dosage form size of the API, alone or in combination with another therapeutic agent, as described elsewhere herein. In some embodiments, the dosage form size of the total pharmaceutical formulation is 175 mg. In some embodiments disclosed herein the dosage form size of the total pharmaceutical formulation is 350 mg. In some embodiments disclosed herein the dosage form size of the total pharmaceutical formulation is 700 mg. One skilled in the art will realize that a range of dosage form sizes of the total pharmaceutical formulation can be made and are encompassed by this disclosure. The preferred dosage form size range of the total pharmaceutical formulation is from 50 mg to 1500 mg, more typically from 100 mg to 1000 mg, more typically from 175 mg to 700 mg, with the preferred typical dosage form size of the total pharmaceutical formulation being 175 mg, 350 mg, or 700 mg or within a range defined by any two of the aforementioned amounts.

In some embodiments, the at least one pharmaceutically acceptable excipient can be selected from binders, disintegrants, surfactants, or stabilizers. Any one or more of the excipients (including binders, disintegrants, surfactants, or stabilizers) can be appropriate in the pharmaceutical formulation containing the API, alone or in combination with another therapeutic agent, provided that the API, alone or in combination with another therapeutic agent, is not inactivated by the formulation and the formulation is physiologically compatible and tolerable with oral administration to a subject.

1. Binders

In some embodiments, the at least one pharmaceutically acceptable excipient can comprise at least one or more binders. The at least one or more binders can be used, for example, to impart cohesive qualities to a pharmaceutical formulation comprising the API, alone or in combination with another therapeutic agent, and thus permit the resulting dosage form to remain intact during formulation of capsules, tablets, film coated tablets, caplets, gel caps, pill pellets, or beads, suitable for oral administration to a subject. In some embodiments, the one or more binders are selected from microcrystalline cellulose, gelatin, sugars (including, for example, sucrose, glucose, dextrose and maltodextrin), polyethylene glycol, waxes, natural and synthetic gums, polyvinylpyrrolidone, pregelatinized starch, povidone, cellulosic polymers (including, for example, hydroxypropyl cellulose (HPC), hydroxypropyl methylcellulose (HPMC), methyl cellulose, hydroxyethyl cellulose), or hydroxypropyl cellulose (HPC), or any combinations thereof.

2. Disintegrants

In some embodiments, the at least one pharmaceutically acceptable excipient can comprise one or more disintegrants. The at least one or more disintegrants can be used, for example, to facilitate disintegration of a pharmaceutical formulation after oral administration. In some embodiments, the at least one or more disintegrants are selected from starches, clays, celluloses, algins, gums, or crosslinked polymers or any combinations thereof. In some embodiments, the one or more disintegrants are selected from crosslinked polyvinylpyrrolidone (PVP-XL), sodium starch glycolate, alginic acid, methacrylic acid DYB, microcrystalline cellulose, crospovidone, polacriline potassium, sodium starch glycolate, starch, pregelatinized starch, or croscarmellose sodium or any combinations thereof.

3. Surfactants

In some embodiments, the at least one pharmaceutically acceptable excipient can comprise one or more surfactants. The at least one or more surfactants can be used, for example, as a wetting agent. The at least one or more surfactants can be used, for example, to improve the permeation and/or bioavailability of the API, alone or in combination with another therapeutic agent. In some embodiments, the at least one or more surfactants are selected from anionic surfactants, non-ionic surfactants, or zwitterionic surfactants or any mixture thereof. In some embodiments, the one or more surfactants are selected from poly(oxyethylene) sorbitan fatty acid ester, poly(oxyethylene) stearate, poly(oxyethylene) alkyl ether, polyglycolated glyceride, poly(oxyethylene) castor oil, sorbitan fatty acid ester, poloxamer, fatty acid salt, bile salt, alkyl sulfate, lecithin, mixed micelle of bile salt and lecithin, glucose ester vitamin E TPGS (D-α-tocopheryl polyethylene glycol 1000 succinate), or sodium lauryl sulfate or any combinations thereof.

4. Stabilizers

In some embodiments, the at least one pharmaceutically acceptable excipient can comprise one or more stabilizers. In some embodiments, the at least one or more stabilizers are selected from alkanizing agents, chelating agents, photoprotectants, or antioxidants or any combinations thereof.

In some embodiments, the alkanizing agent is selected from alkali metal salt additives or an alkaline earth metal salt additive or any combinations thereof. Alkali metal salt additives suitable for use in some embodiments can comprise, for example, sodium carbonate, sodium hydroxide, sodium silicate, disodium hydrogen orthophosphate, sodium aluminate or other suitable alkali metal salts or any combinations thereof. Alkaline earth metal salt additives can comprise, for example, calcium carbonate, calcium hydroxide, magnesium carbonate, magnesium hydroxide, magnesium silicate, magnesium aluminate, or aluminum magnesium hydroxide or any combinations thereof.

In some embodiments, the chelating agent comprises disodium EDTA, edetic acid, or citric acid, or any combination thereof.

In some embodiments, a photoprotectant can be used, for example, to protect the pharmaceutical formulation from the chemical or physical effects of light. In some embodiments, the photoprotectant is selected from titanium oxide, ferric oxide, or zinc oxide or any combination thereof.

In some embodiments, the antioxidant is selected from butylated hydroxyanisole (BHA), sodium ascorbate, butylated hydroxytoluene (BHT), sodium sulfite, propyl gallate, tocopherol, citric acid, malic acid, or ascorbic acid, or any mixtures thereof.

In several embodiments, the pharmaceutical formulations described herein further include at least one pharmaceutically acceptable diluent. Specific examples of diluents include e.g. calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, sugar etc.

D. Dosage Forms

In some embodiments, the API, alone or in combination with another therapeutic agent, may be formulated as a pharmaceutical formulation suitable for oral administration to a subject. In some embodiments, the pharmaceutical formulation is formulated for oral ingestion by a subject as a tablet, pill, capsule, granule, gummy, dragee, or liquid form, gel, syrup, slurry, spray, or suspension. In some embodiments, the formulation is in the form of a tablet, a coated tablet, a gel cap, a caplet, a pellet, or a bead. In some embodiments, the pharmaceutical formulation is in the form of a capsule having a dissolvable enclosure for carrying the API, alone or in combination with another therapeutic agent. In one embodiment, a capsule is made of gelatin. In some embodiments, the pharmaceutical formulation is in the form of a soft gel capsule.

Pharmaceutical formulations for oral administration may be obtained by combining the API, alone or in combination with another therapeutic agent, with one or more pharmaceutically acceptable carriers and/or excipients, optionally grinding the resulting mixture, and processing the mixture, to obtain tablets, pills, capsules, granules, dragees, a liquid, a gel, a syrup, a slurry, a spray, or a suspension. The pharmaceutical formulations comprising the API, alone or in combination with another therapeutic agent, may be manufactured by mixing, dissolving, granulating, dragee-making, levigating, emulsifying, encapsulating, entrapping or tablet-forming processes.

In several embodiments, a dosage form of the pharmaceutical formulations can be coated tablets. In some embodiments, the coated tablets include a coating that can be formed from a water insoluble polymer and an enteric polymer. Suitable water insoluble polymers include cellulose derivatives (e.g. ethylcellulose), polyvinyl acetate (Kollicoat SR30D from BASF), neutral copolymers based on ethyl acrylate and methylmethacrylate, copolymers of acrylic and methacrylic acid esters with quaternary ammonium groups, such as Eudragit NE, RS or RS30D, RL or RL30D and the like. The term "enteric polymer" as used herein, is a material that is insoluble at pH levels found in the stomach, and is soluble at pH levels found in the intestinal tract. Suitable enteric polymers include acid substituted cellulose esters (e.g., cellulose acetate phthalate, hydroxypropyl msethylcellulose phthalate, hydroxypropyl methylcellulose acetate succinate), polyvinyl acetate phthalate, pH-sensitive methacrylic acid-methamethacrylate copolymers and shellac. Commercially available enteric polymers suitable for use herein are sold under the trade name "Eudragit" (e.g., Eudragit LI 00, S100, L30D) manufactured by Rhom Pharma, Cellacefate (cellulose acetate phthalate) from Eastman Chemical Co., Aquateric (cellulose acetate phthalate aqueous dispersion) from FMC Corp. and Agoat (hydroxypropyl methylcellulose acetate succinate aqueous dispersion) from Shin Etsu K.K. In several embodiments, the coated tablets include a coating described in U.S. Pat. No. 6,627,223, herein incorporated by reference for all purposes. In several embodiments, the coating and/or the coated tablets can be plasticized. Representative examples of suitable plasticizers that can be used to plasticize the coating and/or the coated tablets include triacetin, tributyl citrate, triethyl citrate, acetyl tri-n-butyl citrate, diethyl phthalate, castor oil, dibutyl sebacate, acetylated monoglycerides and the like or mixtures thereof. In one embodiment, the dosage forms may include one or more different types of delayed release beads, e.g., delayed release beads with different delayed release layers, or with different combinations of sealant and/or enteric layers. For example, delayed release beads having different delayed release layers can exhibit different release rate characteristics, thereby providing the dosage form with different overall drug release characteristics. In several embodiments, the pharmaceutical formulations comprise capsules, e.g., gelatin or HPMC capsules. In several embodiments, the dosage forms release the API over a period equal to or greater than about 0.1, 0.25, 0.5, 0.75, 1, 1.25, 1.5, 1.75, 2, 2.25, 2.5, 3, 3.5, 4, 4.5, 5, 6, 7, 8, 9, 10 h, or ranges including and/or spanning the aforementioned values. In several embodiments, the dosage forms release the API for about 0.25 to about 5 h, or about 0.5 to about 3 h, or about 0.5 to about 1.25 h. The drug release profile for the pharmaceutical formulations described herein can be evaluated in vitro using various dissolution testing methods, such as United States Pharmacopocia Apparatus 1 (baskets@ 100 rpm) or Apparatus 2

(paddles @ 50 rpm) and a two-stage dissolution methodology, testing initially in 700 mL of 0.1N HCl for and then in 900 mL at pH 6.8. Drug/acid-release with time is determined by HPLC on samples obtained at selected intervals.

In some embodiments, the coated tablets can include a film coating can comprise, for example, a film-forming polymer, or a plasticizer. Non-limiting examples of film-forming polymers suitable for use in the embodiments described herein comprise hydroxypropyl methylcellulose, hydroxypropyl cellulose, methylcellulose, polyvinyl pyrrolidine, or starches or any combinations thereof. Non-limiting examples of plasticizers suitable for use in the embodiments described herein comprise polyethylene glycol, tributyl citrate, dibutyl sebecate, or acetylated monoglyceride or any combinations thereof. Dyestuffs or pigments may be added to the pharmaceutical formulation or to coatings for the pharmaceutical formulation for identification or to characterize different combinations of active compound doses. For this purpose, concentrated sugar solutions may be used, which may optionally comprise gum arabic, talc, polyvinyl pyrrolidone, carbopol gel, polyethylene glycol, and/or titanium dioxide, lacquer solutions, and suitable organic solvents or solvent mixtures or any combinations thereof. Dyestuffs or pigments may be added for identification or to characterize different dosage amounts of the API, alone or in combination with another therapeutic agent. Non-limiting examples of dyestuffs and pigments suitable for use in the embodiments described herein comprise iron oxides of various colors, lake dyes of many colors, or titanium dioxide or any combinations thereof.

In several embodiments, a dosage form of the pharmaceutical formulations can be a liquid form. Non-limiting examples of suitable liquid forms include liquid suspension, gel, syrup, and slurry.

In some embodiments, the API, alone or in combination with another therapeutic agent, may be formulated as a pharmaceutical formulation suitable for administration to a subject rectally, transmucosally, topically, via intestinal administration, parenteral delivery (including intramuscular, subcutaneous, intravenous, and/or intramedullary injections), intrathecally, via direct intraventricular, intraperitoneal, intranasal, or intraocular injection.

In some embodiments, the pharmaceutical formulation is formulated for intranasal administration. In some embodiments, the formulation is formulated as a drop, a spray, or an inhalant for administration to the nasal cavity. In some embodiments, the API is formulated for intranasal administration alone the API, alone or in combination with another therapeutic agent, and one or more appropriate pharmaceutically acceptable carriers and/or excipients for intranasal administration.

In some embodiments, the pharmaceutical formulation is formulated for parenteral administration. In some embodiments, the formulation is formulated as a solution for intraperitoneal, infusion, intramuscular, subcutaneous, intradermal, or intravenous injection. In some embodiments, the API is formulated for parenteral administration, alone or in combination with another therapeutic agent, and one or more appropriate pharmaceutically acceptable carriers and/or excipients for parenteral administration.

The pharmaceutical formulation may be presented in a pack or dispenser device, which may contain one or more unit dosage forms of the API, alone or in combination with another therapeutic agent. The pack may for example include metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. The pharmaceutical formulation comprising the API, alone or in combination with another therapeutic agent, may be placed in an appropriate container, and labeled for treatment or inhibition of an indicated condition, such as for treatment or inhibition of a cancer such as bladder cancer or prostate cancer.

In some embodiments, the pharmaceutical formulations comprising the API, alone or in combination with another therapeutic agent, can be stable for at least, 1 week, 2 weeks, 3 weeks, 1 month, 2 months, 3 months, 6 months, 9 months, 12 months, 15 months, 18 months, 24 months, 36 months, or 48 months or within a range defined by any two of the aforementioned times.

In several embodiments, the pharmaceutical formulations inhibit the growth or delays the onset of melanoma. In several embodiments, the pharmaceutical formulations reduce melanoma tumor size. In several embodiments, the pharmaceutical formulations inhibit the growth or delays the onset of a leukemia. In several embodiments, the pharmaceutical formulations reduce leukemia cancer mass.

Methods of Treating Cancer

Several embodiments of the present disclosure relate to methods for treating a cancer or a tumor. In several embodiments, the methods are for the treatment of cancer. In other embodiments, the methods are for the treatment of a tumor. The methods include selecting or identifying a subject having a population frequency of myeloid derived suppressor cells (MDSCs) greater than or equal to about 3%. As used herein, the term "population frequency" has its ordinary meaning as understood in light of the specification and is a percentage of HLA-DR$^{low/-}$ cells among CD14$^{+}$CD11b$^{+}$ monocytes. As used herein, the terms "myeloid derived suppressor cells" and "MDSCs" are a heterogeneous population of cells that expands during cancer, inflammation and infection, and has the ability to suppress T-cell responses. MDSCs regulate the immune response both for individuals with diseases and for healthy individuals. MDSCs can be classified as monocytic myeloid derived suppressor cells (m-MDSCs) and polymorphonuclear myeloid derived suppressor cells (pmn-MDSCs). The methods include administering to the subject the pharmaceutical formulation that includes a therapeutically effective amount of at least one active pharmaceutical ingredient (API). In several embodiments, the API includes histamine, a histamine salt, a histamine derivative, a salt of a histamine derivative, and any combination of the foregoing. In some embodiments, the API is histamine. In certain embodiments, the API is a histamine salt. In other embodiments, the API is a histamine derivative. In other embodiments, the API is a salt of a histamine derivative. In several embodiments, the pharmaceutical formulations include a pharmaceutically acceptable carrier, a pharmaceutically acceptable excipient, a pharmaceutically acceptable diluent, and any combination of the foregoing. In several embodiments, the pharmaceutical formulation comprises a dosage form selected from a coated tablet and a liquid form.

In several embodiments, the subject has a cancer or a tumor. In several embodiments, the subject's population frequency of MDSCs is greater than or equal to about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 60%, or ranges including and/or spanning the aforementioned values.

In several embodiments, the MDSCs comprise m-MDSCs. In several embodiments, the subject's population frequency of m-MDSCs can be a percentage of HLA-DR$^{low/-}$ cells among CD14$^{+}$CD11b$^{+}$ monocytes. In several embodiments, the subject's population frequency of m-MDSCs is from about 3% to about 60%, such as greater than or equal to about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 60%, or ranges including and/or spanning the aforementioned values. In several embodiments, the MDSCs comprise pmn-MDSCs. In several embodiments, the subject's population frequency of pmn-MDSCs is greater than or equal to about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 60%, or ranges including and/or spanning the aforementioned values.

In several embodiments, the subject can have received checkpoint inhibitor therapy or can be receiving ongoing checkpoint inhibitor therapy. The term "checkpoint inhibitor therapy," as used herein, is a treatment that includes administration of at least one immune checkpoint inhibitor, as described elsewhere herein. In some embodiments, the subject has no response to checkpoint inhibitor therapy. In other embodiments, the subject has an incomplete response to checkpoint inhibitor therapy. The checkpoint inhibitor therapy can include a small molecule that targets programmed cell death protein 1 (PD-1), programmed death ligand 1 (PD-L1), cytotoxic T-lymphocyte-associated protein 4 (CTLA-4), and any combination of the foregoing. In several embodiments, the small molecule can be an immune checkpoint inhibitor selected from pembrolizumab, nivolumab, ipilimumab, and any combination of the foregoing.

In several embodiments, the selecting or identifying is accomplished by a detection assay. The detection assay can be an assay that has been cleared by the United States Food and Drug Administration (FDA) for the detection of MDSCs. In several embodiments, the assay can be interpreted in a diagnostic laboratory that is certified under the Clinical Laboratory Improvement Amendments of 1988 (CLIA).

In several embodiments, the methods inhibit the production or release of intracellular hydrogen peroxide. In several embodiments, the methods inhibit the production or release of intracellular hydrogen peroxide by monocytes. In an embodiment, the inhibition occurs when the API binds histamine H2 receptors. In several embodiments, the inhibition occurs when the API binds histamine H2 receptors selectively. In several embodiments, the methods have an affinity for histamine H2 receptors that is higher compared to the affinity for any other histamine receptor. In several embodiments, the methods have an affinity for histamine H2 receptors that is higher compared to the affinity for a H1 receptor, a H3 receptor, a H4 receptor, and any combination of the foregoing.

In several embodiments, the methods decrease a level of reactive oxygen species (ROS) within the subject.

In several embodiments, the methods inhibit NADPH oxidase isoform activity.

Natural killer (NK) cells have a critical role in the tumor microenvironment (TME) associated with cancer development and progression. Within the TME, cells from adaptive and innate immune system, including NK cells, are one of the most abundant components. The dynamic interactions between immune and cancer cells create complex molecular mechanisms that can deactivate NK cells and sustain tumor growth. In several embodiments, the method avoids inactivation of natural killer cells in the tumor micro-environment. In several embodiments, the method increases activation of natural killer cells in the tumor micro-environment.

In several embodiments, the methods include administering another therapeutic agent. In several embodiments, the other therapeutic agent is selected from an immune checkpoint inhibitor, a cancer immunotherapy agent, a chemotherapy agent, radiation, surgery, and any combination of the foregoing.

In several embodiments, the methods include administering an immune checkpoint inhibitor. The immune checkpoint inhibitor can be a chemical compound (e.g., small molecule) or other entity that targets (i.e., blocks or otherwise inhibits) PD-1, PD-L1, CTLA-4, and any combination of the foregoing In several embodiments, the immune checkpoint inhibitor can be selected from pembrolizumab, nivolumab, ipilimumab, and any combination of the foregoing.

In several embodiments, the methods include administering at least one cytokine. The cytokine can be selected from chemokines, interferons, interleukins, lymphokines, tumor necrosis factors, and any combination of the foregoing.

In several embodiments, the methods include administering at least one interleukin. The interleukin can be selected from IL-1, IL-1α, IL-1β, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, and any combination of the foregoing.

In several embodiments, the pharmaceutical formulation, alone or in combination with another therapeutic agent, is administered orally. In several embodiments, the pharmaceutical formulation, alone or in combination with another therapeutic agent, is administered parenterally. In several embodiments, the pharmaceutical formulation, alone or in combination with another therapeutic agent, is administered subcutaneously.

In several embodiments, the cancer or the tumor is selected from a leukemia, a myeloma, a bone marrow cancer, a Hodgkin's lymphoma, a Non-Hodgkin's lymphoma, a follicular lymphoma, a lymphoid malignancy of T-cell or B-cell origin, a bladder cancer, a brain cancer, a breast cancer, a cervical cancer, a colorectal cancer, an esophageal cancer, a hepatocellular cancer, a melanoma, a head and neck cancer (including oral cancer), an ovarian cancer, a small cell lung cancer, a non-small cell lung cancer, a prostate cancer, a spleen cancer, a polycythemia vera, a thyroid cancer, an endometrial cancer, a stomach cancer, a gallbladder cancer, a bile duct cancer, a testicular cancer, a neuroblastoma, an osteosarcoma, a sarcoma, a carcinoma, an Ewing's tumor and a Wilms's tumor.

In several embodiments, the cancer is a melanoma. In several embodiments, the methods inhibit the growth or delays the onset of melanoma. In several embodiments, the methods reduce a melanoma tumor size.

In several embodiments, the cancer is a leukemia. In several embodiments, the cancer is a leukemia selected from an acute myeloid leukemia, a lymphoblastic leukemia, a myelogenous leukemia, a chronic lymphocytic leukemia, a chronic myeloid leukemia, and any combination of the foregoing. In several embodiments, the methods inhibit the growth or delays the onset of leukemia. In several embodiments, the methods reduce a leukemia tumor size.

Some embodiments relate to the use of an effective amount of the pharmaceutical formulation of the present disclosure in the manufacture of a medicament for treating a cancer or a tumor. Other embodiments relate use of an effective amount of the pharmaceutical formulation of the present disclosure in the manufacture of a medicament for treating a malignant growth or a tumor. Certain embodiments relate use of an effective amount of the pharmaceutical formulation of the present disclosure in the manufacture of a medicament for inhibiting replication of a malignant growth or a tumor. In several embodiments, the use further comprises administering the pharmaceutical formulation orally.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The above description discloses several methods and materials of the present disclosure. This disclosure is susceptible to modifications in the methods and materials, as well as alterations in the fabrication methods and equipment. Such modifications will become apparent to those skilled in the art from a consideration of this disclosure or practice of the disclosure disclosed herein. Consequently, it is not intended that this disclosure be limited to the specific embodiments disclosed herein, but that it covers all modifications and alternatives coming within the true scope and spirit of the disclosure.

EXAMPLES

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. Changes therein and other uses which are encompassed within the spirit of the disclosure as defined by the scope of the claims will occur to those skilled in the art.

Example 1

Effects on NK Cell Function

This is a prophetic example. The effect of a pharmaceutical formulation containing histamine dihydrochloride described herein on NK cell function is evaluated using an in vivo mouse model assay. The levels of radioactivity in lungs has been shown to be inversely proportional to NK cell function in that the greater the lysis by NK cells of the target YAC-1 cells the less radioactivity is shown in the lungs. Mice are injected with a solution of the pharmaceutical formulation, ranitidine or a control solution. Twenty-four hours later they are injected intravenously with $^{51}$Cr-labeled YAC-1 lymphoma cells which form tumor emboli in the lungs and which are extremely sensitive to lysis by NK cells. Four hours after the YAC-1 injection the animals are sacrificed and the radioactivity present in their lungs is measured. Treatment with the pharmaceutical formulation reduces the amount of lung radioactivity by up to ⅔ when compared to the control group. Treatment with the H2 antagonist, ranitidine, results in a tripling of the level of radioactivity.

Example 2

Pharmacodynamic Studies

This is a prophetic example. The pharmaceutical formulation described in Example 1 is administered in various animal tumor models for the pharmacodynamic studies shown in Table 1. The effect of the pharmaceutical formulation on NK sensitive cells and H2 receptor involvement is shown to be most effective when the pharmaceutical formulation is administered 2-6 hours prior to cell inoculation.

TABLE 1

| Tumour model | Species | Dosage | Effects |
|---|---|---|---|
| Fibrosarcoma | Mouse | 6 mg/day i.p., daily | Reduced tumour growth and improved survival |
| Chemically induced gut tumours | Rat | 4 mg/day s.c., daily | Reduced glandular tumour in rats |
| Ascitis sarcoma | Rat | 0.005 μg/day i.p. | Improved survival |
| Chemically induced mammary carcinoma | Rat | 0.1 mg/kg/day s.c., daily | Reduced tumour incidence and growth |
| Melanoma | Mouse | 2.5-250 mg/kg i.v., single dose | Reduced pulmonary metastasis |
| YAC-1 lymphoma | Mouse | 125 mg/kg i.v., single dose | Reduced YAC-1 lung tumour emboli |
| YAC-1 lymphoma | Mouse | 125 mg/kg i.v., single dose | Improved NK cell clearance of YAC-1 tumour cells |
| Colorectal carcinomas | Mouse | 1 mg/kg/day i.p. daily | Reduced growth of human tumours transplanted to the subrenal capsule |
| Syngeneic colorectal adenocarcinoma | Rat | 0.5 mg/kg/day s.c. daily | Reduced growth rate of transplanted liver tumours in rats |
| Leydig cell sarcoma | Rat | 0.5 mg/kg/day s.c. daily | Reduced growth rate of transplanted liver tumours in rats |

TABLE 1-continued

| Tumour model | Species | Dosage | Effects |
|---|---|---|---|
| Colorectal cancer | Mouse | Local administration via osmotic pump | Enhanced tumour growth |
| Leukaemia | Mouse | 5 μg/day; i.p. daily for 5 days | Slightly increased survival in mice inoculated with murine B-cell leukaemia |

Note:
i.p. = intraperitoneal;
i.v. = intravenous;
s.c. = subcutaneous

Example 3

Combination Therapy with IL-2 in Animal Models

This is a prophetic example. Interleukin-2 is administered in combination with the pharmaceutical formulation described in Example 1 in various animal tumor models for the studies shown in Table 1. IL-2 only weakly activates NK cells or T cells in an environment of oxidative stress. The pharmaceutical formulation inhibits production of reactive oxygen species and protects NK cells and T cells from down-regulation and apoptosis thereby improving the IL-2-induced activation of T cells and NK cells in tumors. The combined treatment effectively protects mice against B16 melanoma lung metastases.

TABLE 2

| Tumour model | Species | Effects |
|---|---|---|
| B16 melanoma | Mouse | Potentiate reduction of metastatic lung tumours by IL-2 |
| YAC-1 lymphoma | Mouse | Enhance NK cell mediated clearance of YAC-1 cells from lungs by IL-2 |
| Dunning prostate adenocarcinoma | Rat | Potentiate anti-tumour properties of IL-2 |
| Intra-cerebral glioma | Rat | Reduce growth of established intracerebral tumours by 50% |

Example 4

Treatment of Leukemia

Interleukin-2 (IL-2) administered in combination with the pharmaceutical formulation described in Example 1 is an immunotherapy which aims to induce immune-mediated destruction of residual myeloid leukemia cells and thereby to prevent relapse of leukemia. The role of histamine dihydrochloride is to protect lymphocytes, in particular NK cells and T cells, which are responsible for the immune-mediated destruction of residual leukemic cells. The role of IL-2 is to promote the functions of NK cells and T cells by activating the anti-leukemic properties of these cells and by expanding these cell populations by inducing cell cycle proliferation. The mechanism by which the histamine dihydrochloride improves the anti-leukemic function of lymphocytes in AML is considered to be by inhibition of reactive oxygen species (ROS or 'oxygen free radicals'), which are synthesized by monocytes/macrophages and granulocytes. ROS are known to limit the anti-leukemic effects of lymphocyte activators such as IL-2, by triggering dysfunction and death by apoptosis in NK cells and T cells. Histamine dihydrochloride inhibits NAPDH oxidase which initiates the formation and release of ROS from phagocytes. By inhibiting oxidase function and reducing ROS production, the histamine dihydrochloride protects IL-2-activated NK cells and T cells from oxygen free radical-induced inhibition and apoptosis.

This is a prophetic example. Recombinant Interleukin-2 (aldesleukin, IL-2) is administered at a dosage of 16,400 IU/kg (1 μg/kg) twice daily as a subcutaneous injection. The pharmaceutical formulation described in Example 1 is orally administered in a dosage of 5 mg from 1 to 3 minutes after each injection of IL-2. The dual therapy is administered for 10 treatment cycles: each cycle consists of a treatment period of 21 days (3 weeks) followed by a three-week or six-week treatment-free period. For cycles 1-3, each cycle consists of 3 weeks of treatment, followed by a 3-week treatment free period. For cycles 4-10, each cycle consists of 3 weeks of treatment, followed by a 6-week treatment free period. The 10 treatment cycles are completed over an 81-week period.

In a first study, the participants are 261 individual patients in a first remission from leukemia. The study participants are split into a group of experimental patients and control patients. The experimental patients are administered the dual therapy for 10 treatment cycles over 81 weeks. The control group receives a placebo containing magnesium stearate in the same treatment cycle and duration. The median duration of leukemia-free survival is 291 days (9.7 months) in the control patients and 450 days (15 months) in the experimental patients.

In a second study, the participants are 59 individual patients in a subsequent remission from leukemia after relapse. The study participants are split into a group of experimental patients and control patients. The experimental patients are administered the dual therapy for 10 treatment cycles over 81 weeks. The control group receives a placebo containing magnesium stearate in the same treatment cycle and duration. The number of in the experimental patients remaining leukemia-free for 3 years is 26% in the control patients and 40% in the experimental patients.

Example 5

Treatment of Melanoma

This is a prophetic example. The participants of the study are 16 melanoma patients having a population frequency of MDSCs between 15% and 21% as determined by an FDA-cleared MDSC detection assay conducted in a diagnostic laboratory that is certified under the Clinical Laboratory Improvement Amendments of 1988 (CLIA). The study participants are split into a group of experimental patients and control patients. The pharmaceutical formulation described in Example 1 is administered to the experimental patients by subcutaneous injection. The control group receives a placebo containing magnesium stearate in the same treatment cycle and duration. The median duration of melanoma-free survival is 610 days in the experimental patients and 270 days in the control patients.

What is claimed is:

1. A method for treating a melanoma, the method comprising:

selecting or identifying a subject having a population frequency of myeloid derived suppressor cells (MDSCs) greater than or equal to about 15%, wherein the population frequency comprises a percentage of HLA-$DR^{low/-}$ cells among $CD14^{+}CD11b^{+}$ monocytes; and administering to the subject a pharmaceutical formulation comprising:

a therapeutically effective amount of an active pharmaceutical ingredient (API), wherein the API comprises histamine, a histamine salt, a histamine derivative, a salt of a histamine derivative, or any combination of the foregoing, wherein the histamine derivative comprises a $C_{1-6}$ alkyl histamine, and wherein the salt of the histamine derivative comprises a $C_{1-6}$ alkyl histamine monocation or a $C_{1-6}$ alkyl histamine polycation; and at least one of a pharmaceutically acceptable carrier, a pharmaceutically acceptable excipient, a pharmaceutically acceptable diluent, and any combination of the foregoing, wherein the pharmaceutical formulation comprises a dosage form selected from a coated tablet and a liquid form.

2. The method of claim 1, wherein the subject has a cancer or a tumor.

3. The method of claim 1, wherein the MDSCs comprise monocytic myeloid derived suppressor cells (m-MDSCs).

4. The method of claim 1, wherein the population frequency is from 15% to 21%.

5. The method of claim 1, wherein the subject has an incomplete response to checkpoint inhibitor therapy, wherein the checkpoint inhibitor therapy targets programmed cell death protein 1 (PD-1), programmed death ligand 1 (PD-L1), cytotoxic T-lymphocyte-associated protein 4 (CTLA-4), and any combination of the foregoing.

6. The method of claim 1, wherein the selecting or identifying is accomplished by a detection assay.

7. The method of claim 6, wherein the detection assay has been cleared by the United States Food and Drug Administration (FDA) for the detection of MDSCs.

8. The method of claim 6, wherein the detection assay is interpreted in a diagnostic laboratory that is certified under the Clinical Laboratory Improvement Amendments of 1988 (CLIA).

9. The method of claim 1, wherein the method inhibits the production or release of intracellular hydrogen peroxide.

10. The method of claim 1, wherein the method decreases a level of reactive oxygen species (ROS) within the subject.

11. The method of claim 1, wherein the method inhibits NADPH oxidase isoform activity.

12. The method of claim 1, wherein the method avoids inactivation of natural killer cells in the tumor micro-environment, or wherein the method increases activation of natural killer cells in the tumor micro-environment.

13. The method of claim 1, wherein the method further comprises administering another therapeutic agent.

14. The method of claim 13, wherein the other therapeutic agent is selected from an immune checkpoint inhibitor, a cancer immunotherapy agent, a chemotherapy agent, radiation, surgery, and any combination of the foregoing.

15. The method of claim 14, wherein the other therapeutic agent comprises an immune checkpoint inhibitor selected from pembrolizumab, nivolumab, ipilimumab, and any combination of the foregoing.

16. The method of claim 15, wherein the method further comprises administering at least one cytokine, or administering at least one interleukin.

17. The method of claim 1, wherein the pharmaceutical formulation is administered orally, parenterally, subcutaneously, or transmucosally.

18. The method of claim 17, wherein the pharmaceutical formulation is administered orally to the buccal lining.

19. The method of claim 1, wherein the method inhibits the growth or delays the onset of melanoma.

20. The method of claim 1, wherein the method reduces melanoma tumor size.

* * * * *